US012667532B2

(12) United States Patent
Frantz et al.

(10) Patent No.: US 12,667,532 B2
(45) Date of Patent: Jun. 30, 2026

(54) ENHANCED DEPOSITION COMPOSITIONS FOR PERSONAL CARE ACTIVES

(71) Applicant: Lubrizol Advanced Materials, Inc., Cleveland, OH (US)

(72) Inventors: Seren Frantz, Scotch Plains, NJ (US); Michael Knopf, Hackettstown, NJ (US); Yi Yang, Bridgewater, NJ (US); Robert Jacobs, Olmsted Falls, OH (US); Carole A. Lepilleur, Akron, OH (US)

(73) Assignee: Lubrizol Advanced Materials, Inc., Cleveland, OH (US)

( * ) Notice: Subject to any disclaimer, the term of this patent is extended or adjusted under 35 U.S.C. 154(b) by 468 days.

(21) Appl. No.: 18/032,907

(22) PCT Filed: Oct. 21, 2021

(86) PCT No.: PCT/US2021/055946
§ 371 (c)(1),
(2) Date: Apr. 20, 2023

(87) PCT Pub. No.: WO2022/087199
PCT Pub. Date: Apr. 28, 2022

(65) Prior Publication Data

US 2023/0404895 A1 Dec. 21, 2023

Related U.S. Application Data

(60) Provisional application No. 63/094,631, filed on Oct. 21, 2020.

(51) Int. Cl.

| | |
|---|---|
| ***A61K 8/46*** | (2006.01) |
| ***A61K 8/73*** | (2006.01) |
| ***A61K 8/81*** | (2006.01) |
| ***A61K 8/92*** | (2006.01) |
| ***A61Q 5/00*** | (2006.01) |
| ***A61Q 5/02*** | (2006.01) |
| ***A61Q 19/00*** | (2006.01) |
| ***C07K 16/00*** | (2006.01) |

(52) U.S. Cl.
CPC ............ *A61K 8/731* (2013.01); *A61K 8/8147* (2013.01); *A61K 8/922* (2013.01); *A61Q 5/00* (2013.01); *A61Q 19/00* (2013.01); *C07K 16/00* (2013.01); *A61K 2800/5424* (2013.01); *A61K 2800/5428* (2013.01); *A61K 2800/596* (2013.01)

(58) Field of Classification Search
None
See application file for complete search history.

(56) References Cited

U.S. PATENT DOCUMENTS

| | | | | |
|---|---|---|---|---|
| 3,929,678 | A | 12/1975 | Laughlin et al. | |
| 4,565,647 | A | 1/1986 | Llenado | |
| 5,456,849 | A | 10/1995 | Houghton et al. | |
| 5,554,408 | A | 9/1996 | Cain et al. | |
| 5,720,964 | A | 2/1998 | Murray | |
| 5,858,948 | A | 1/1999 | Ghosh et al. | |
| 6,555,100 | B1 | 4/2003 | Restle et al. | |
| 7,115,550 | B2 | 10/2006 | Szewczyk | |
| 10,143,644 | B2 * | 12/2018 | Gevgilili | A61K 8/37 |
| 10,159,638 | B2 | 12/2018 | Fevola et al. | |
| 2014/0219945 | A1 * | 8/2014 | Meralli | A61K 8/9794 424/70.12 |
| 2017/0056315 | A1 * | 3/2017 | Gevgilili | A61K 8/416 |

FOREIGN PATENT DOCUMENTS

| | | | |
|---|---|---|---|
| EP | 1447075 | | 11/2013 |
| EP | 2964181 | | 1/2016 |
| JP | 2000-510877 | A2 | 8/2000 |
| JP | 2003-535045 | A2 | 11/2003 |
| WO | 9921530 | | 5/1999 |
| WO | 0176543 | | 10/2001 |
| WO | WO2001074311 | A2 | 10/2001 |
| WO | 2011127364 | | 10/2011 |
| WO | 2016178660 | | 11/2016 |

* cited by examiner

*Primary Examiner* — Brian Gulledge
(74) *Attorney, Agent, or Firm* — Michael A. Miller

(57) ABSTRACT

The present technology relates to compositions suitable for depositing personal care actives onto keratinous substrates. More particularly, the technology concerns compositions comprising lipophilic materials which are deposited from an ampholytic-anionic delivery system. The compositions exhibit high deposition of the lipophilic material onto keratinous substrates such as the skin, nails, and/or hair upon application thereto. In one aspect, the disclosed technology relates to a personal care deposition composition for depositing a lipophilic material onto a keratinous substrate comprising: a) at least one ampholytic polymer; b) at least one anionic polymer; c) at least one lipophilic material; and d) water, wherein the weight ratio of the at least one ampholytic polymer to the at least one anionic polymer ranges from about 10:1 to about 1:1.

31 Claims, No Drawings

ENHANCED DEPOSITION COMPOSITIONS FOR PERSONAL CARE ACTIVES

CROSS REFERENCE TO RELATED APPLICATION

This application claims priority from: PCT Application Serial No. PCT/US2021/055946 filed on Oct. 21, 2021, which claims the benefit of U.S. Provisional Application No. 63/094,631 filed on Oct. 21, 2020, both of which are incorporated in their entirety by reference herein.

TECHNOLOGICAL FIELD

The present technology relates to compositions suitable for depositing personal care actives onto keratinous substrates. More particularly, the technology concerns compositions comprising lipophilic materials which are deposited from an ampholytic-anionic delivery system. The compositions exhibit high deposition of the lipophilic material onto keratinous substrates such as the skin, nails, and/or hair upon application thereto. The deposition composition of the present technology comprises a) at least one ampholytic polymer; b) at least one anionic polymer; and c) at least one lipophilic material that is deposited onto the keratinous substrate when the deposition composition is applied to the substrate.

BACKGROUND

It is well-known in the industry that the delivery of active ingredients from personal care formulations, particularly those containing detersive surfactants, is a challenge. Many conventional personal care products, including rinse-off cleansers, are relatively ineffective in depositing the actives contained in the product to the keratinous surfaces of the human body in desirably high amounts. The use of conventional rinse-off products results in most of the active agent being washed away with relatively low amounts being left on the scalp, hair, skin and nails. By their very nature, these products are designed to cleanse sebum and other environmental particulates from body surfaces rather than promote the deposition of actives on same.

Many suffer from skin conditions that result in dryness, discoloration, edema, pain and general irritation. Some of these conditions are elicited by topical cleansing products including shampoos, body cleansers and other personal care products that contain harsh detersive surfactants. Detersive surfactants remove some of the skin's protective lipids and/or secretions which can increase the irritation and sensitivity of the skin.

There remains a need to optimize the level of actives, including lipophilic materials, deposited onto the keratinous surfaces of the human body from surfactant containing cleansing compositions. By providing the benefits of lipophilic deposition the negative impacts of harsh surfactants may be reduced.

SUMMARY OF THE DISCLOSED TECHNOLOGY

In one aspect, the disclosed technology relates to a personal care deposition composition for depositing a lipophilic material onto a keratinous substrate comprising:

a) from about 0.03 to about 2 wt. %, or from about 0.1 to about 0.8 wt. %, or from about 0.2 to about 0.6 wt. % of at least one ampholytic polymer;

b) from about 0.01 to about 2 wt. %, or from about 0.05 to about 0.5 wt. %, or from about 0.1 to about 0.3 wt. % of at least one anionic polymer;

c) from about 0.01 wt. % to about 45 wt. %, or from about 0.05 to about 40 wt. %, or from about 0.1 to about 30 wt. %, or from about 0.5 to about 25 wt. %, or from about 1 to about to about 20 wt. %, or from about 3 to about 15 wt. %, or from about 5 to about 10 wt. % of at least one lipophilic material;

d) from about 30 to about 95 wt. %, or from about 50 to about 90 wt. %, or from about 70 to about 85 wt. % water; wherein the weight ratio of ampholytic polymer to anionic polymer is from about 10:1 to about 1:1, or from about 7:1 to about 2:1, or from about 5:1 to about 3:1; and wherein all weight percent ranges are based on the total weight of the composition and the sum of all components in the composition total 100 wt. %.

DETAILED DESCRIPTION OF THE DISCLOSED TECHNOLOGY

In all aspects of the disclosed technology, all weight percentages are calculated on the weight of the total composition.

Unless otherwise specified, all ratios are expressed as weight ratios.

All numerical ranges of amounts are inclusive and combinable unless otherwise specified.

While overlapping weight ranges for the various components and ingredients that can be contained in the disclosed compositions have been expressed for selected embodiments and aspects of the disclosed technology, the amount of each component in the disclosed compositions is selected from its disclosed range such that the sum of all components or ingredients in the composition will total 100 weight percent. The amounts employed will vary with the purpose and character of the desired product and can be readily determined by one skilled in the art.

The personal care deposition compositions of the disclosed technology may suitably comprise, consist essentially of, or consist of, the components, elements, and process delineations described herein. The disclosed technology illustratively disclosed herein suitably may be practiced in the absence of any element which is not specifically disclosed herein.

The term "personal care" as used herein includes, without being limited thereto, includes cosmetics, toiletries, cosmeceuticals, beauty aids, insect repellents, sun screens, UV absorbers, creams, lotions, personal hygiene and cleansing products (e.g., shampoos, conditioning shampoos, anti-dandruff shampoos, rinse-off conditioners, body-washes, shower creams, shower lotions, shower gels, exfoliating compositions, liquid hand soaps and washes, facial scrubs, facial washes, astringent lotions, skin toners or fresheners, bubble baths, soluble bath oils, and the like) applied to the body, including the skin, hair, scalp, and nails of humans and animals.

The prefix "(meth)acryl" includes "acryl" as well as "methacryl". For example, the term "(meth)acrylic acid" includes both acrylic acid and methacrylic acid.

The term "monomer residue" as used herein refers to a repeating unit within a polymer chain derived from a parent monomer.

The term "lipophilic material" includes any water insoluble, oil miscible, or lipophilic substance which benefits the keratinous substrate, e.g., the skin, hair and nails.

Ampholytic Polymer Component

In one aspect, the personal care deposition composition of the present technology comprises at least one ampholytic polymer comprising repeating units containing cationic groups and repeating units containing anionic groups.

In one aspect, the ampholytic polymer comprises repeating units containing cationic groups, repeating units containing anionic groups and nonionic repeating units.

In addition to or in lieu of repeating units containing cationic and anionic groups, the ampholytic polymer may comprise repeating units containing cationic and anionic ionizable groups. An ionizable group is any cationic and anionic precursor group that can be made cationic by neutralization with an acid (e.g., a cationic group) or anionic by neutralization with a base (e.g., an anionic group).

By "nonionic" is meant that the repeating unit is devoid of ionic or ionizable groups ("nonionizable").

In one aspect, the amount of anionic monomer residues present in the ampholytic polymer is equal to or less than the amount of cationic monomer residues present in the polymer.

In one aspect, the mole ratio of anionic monomer residues to cationic monomer residues in the ampholytic polymer ranges from about 1:15 to about 3:1, or from about 1:10 to about 2:1, or from about 1:5 to 1:1.

In one aspect, the mole ratio of nonionic monomer residues to the combined mole ratio of the anionic and cationic monomer residues in the ampholytic polymer ranges from about 1:20 to about 9:1, or from about 3:7 to about 7:3, or from about 4:6 to about 6:4.

In one aspect, the anionic monomer residue present in the ampholytic polymer is derived from acrylic acid (AA), methacrylic acid (MAA), 2-acrylamido-2-methylpropane sulfonic acid (AMPSA), 2-methacrylamido-2-methylpropane sulfonic acid (MAMPSA), acrylamidomethylpropyl sulfonic acid, and mixtures thereof.

In one aspect, the anionic functional group may comprise a counterion. The counterion can be a proton, an ammonium ion, an organic cation, e.g., an alkanolamine including monoethanolamine, diethanolamine and triethanolamine, an alkali metal cation, e.g., sodium, potassium and lithium, or an alkaline earth metal cation, e.g., calcium and magnesium; and combinations thereof.

In one aspect, the cationic monomer residue present in the ampholytic polymer is derived from diallyldimethylammonium chloride (DADMAC), acrylamidopropyltrimethyl ammonium chloride (APTAC) methacrylamidopropyltrimethylammonium chloride (MAPTAC), and mixtures thereof.

In one aspect, the nonionic monomer residue present in the ampholytic polymer component of the present technology is derived from methyl acrylate (MA), methyl methacrylate, acrylamide (AcAm), methacrylamide, and mixtures thereof.

In one aspect, the ampholytic polymer may be selected from from poly(diallyldimethylammonium chloride-co-acrylic acid) (PQ-22), poly(acrylamide-co-acrylic acid-co-diallyldimethylammonium chloride) (PQ-39), poly(methyl acrylate-co-acrylic acid-co-methacrylamidopropyltrimethyl ammonium chloride) (PQ-47), poly(acrylamide-co-acrylic acid-co-methacrylamidopropyltrimethyl ammonium chloride) (PQ-53), and mixtures thereof.

The foregoing ampholytic polymers may further be classified by their INCI names (International Nomenclature of Cosmetic Ingredients) as Polyquaternium-22, Polyquaternium-39, Polyquaternium-47 and Polyquaternium-53. Mixtures of these Polyquaternium ampholytic polymers may be used.

The ampholytic polymer can be prepared using polymerization techniques that are well-known to a person skilled in the art. These known polymerization techniques include solution polymerization, gel polymerization, precipitation polymerization, inverse emulsion polymerization, aqueous emulsion polymerization, suspension polymerization and micellar polymerization.

A non-limiting list of commercially available ampholytic polymers are marketed under the Merquat™ tradename by Lubrizol Advanced Materials, Inc. as follows.

Ampholytic Polymers

| Merquat Product Designation | Monomer Residues | Monomer Residue Ratio (mole %) | INCI Name |
|---|---|---|---|
| 280 | AA/DADMAC | 36/64 | Polyquaternium-22 |
| 3330PR | AcAm/AA/DADMAC | 35/34/31 | Polyquaternium-39 |
| 3940 | AcAm/AA/DADMAC | 40/31/29 | Polyquaternium-39 |
| 3331PR | AcAm/AA/DADMAC | 51/23/27 | Polyquaternium-39 |
| 2001 | MA/AA/MAPTAC | 10/45/45 | Polyquaternium-47 |
| 2003PR | AcAm/AA/MAPTAC | 50/10/40 | Polyquaternium-53 |

In one aspect, the deposition compositions of the present technology comprise from about 0.03 to about 2 wt. %, or from about 0.1 to about 0.8 wt. %, or from about 0.2 to about 0.6 wt. % of the at least one ampholytic polymer, based on the total weight of the composition.

Anionic Polymer Component

In one aspect, the personal care deposition compositions of the present technology comprise at least one anionic polymer selected from a synthetically derived anioinic polymer, a naturally derived anionic polymer, a derivatized naturally derived anionic polymer, and combinations thereof.

In one aspect, the personal care deposition compositions of the present technology comprise at least one synthetically derived anionic polymer comprising repeating units having at least one carboxylic acid group derived from one or more monoethylenically unsaturated $C_3$-$C_6$ carboxylic acid containing monomer or an anhydride thereof.

In one aspect, the at least one synthetically derived anionic polymer is a linear or crosslinked homopolymer or copolymer derived from a monoethylenically unsaturated $C_3$-$C_6$ carboxylic acid containing monomers or an anhydride thereof.

In one aspect, the synthetically derived anionic polymer is a linear or crosslinked copolymer derived from a monoethylenically unsaturated $C_3$-$C_6$ carboxylic acid containing monomer or an anhydride thereof and one or more monomers of formula (I) and/or formula (II):

(I)

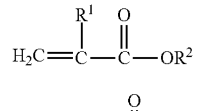

(II)

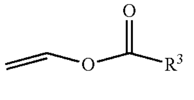

wherein $R^1$ is hydrogen, methyl or ethyl and $R^2$ is an alkyl group containing 1 to 30 carbon atoms.

Exemplary monoethylenically unsaturated $C_3$-$C_6$ carboxylic acid group containing monomers suitable for preparing the anionic homopolymers and copolymers of the present technology include but are not limited to (meth)acrylic acid (i.e., acrylic acid, methacrylic acid), itaconic acid, citraconic acid, maleic acid, fumaric acid, crotonic acid, aconitic acid, and mixtures thereof.

Representative comonomers set forth under formula (I) for preparing the anionic copolymers of the present technology include but are not limited to methyl (meth)acrylate, ethyl (meth)acrylate, propyl (meth)acrylate, isopropyl (meth)acrylate, butyl (meth)acrylate, isobutyl (meth)acrylate, methyl ethacrylate, hexyl (meth)acrylate, heptyl (meth) acrylate, octyl (meth)acrylate, 2-ethylhexyl (meth)acrylate, nonyl (meth)acrylate, decyl (meth)acrylate, isodecyl (meth) acrylate, lauryl (meth)acrylate, stearyl (meth)acrylate, behenyl (meth)acrylate, melissyl (meth)acrylate, and mixtures thereof.

Representative comonomers set forth under formula (II) for preparing the anionic copolymers of the present technology include but are not limited to vinyl acetate, vinyl propionate, vinyl butyrate, vinyl isobutyrate, vinyl valerate, vinyl hexanoate, vinyl 2-methylhexanoate, vinyl 2-ethylhexanoate, vinyl iso-octanoate, vinyl nonanoate, vinyl decanoate, vinyl neodecanoate, vinyl versatate, vinyl laurate, vinyl palmitate, vinyl stearate, and mixtures thereof.

In one aspect, the anionic polymers of the present technology are crosslinked. The crosslinking monomer is a compound having two or more ethylenically unsaturated, nonconjugated double bonds. Exemplary polyunsaturated crosslinking monomers include but are not limited to di(meth)acrylate compounds such as ethylene glycol di(meth) acrylate, polyethylene glycol di(meth)acrylate, triethylene glycol di(meth)acrylate, 1,3-butylene glycol di(meth)acrylate, 1,6-butylene glycol di(meth)acrylate, 1,6-hexanediol di(meth)acrylate, neopentyl glycol di(meth)acrylate, 1,9-nonanediol di(meth)acrylate, 2,2'-bis(4-(acryloxy-propyloxyphenyl)propane, and 2,2'-bis(4-(acryloxydiethoxy-phenyl)propane; tri(meth)acrylate compounds such as, trimethylolpropane tri(meth)acrylate, trimethylolethane tri (meth)acrylate, and tetramethylolmethane tri(meth)acrylate; tetra(meth)acrylate compounds such as ditrimethylolpropane tetra(meth)acrylate, tetramethylolmethane tetra(meth) acrylate, and pentaerythritol tetra(meth)acrylate; hexa(meth) acrylate compounds such as dipentaerythritol hexa(meth) acrylate; allyl compounds such as allyl (meth)acrylate, diallylphthalate, diallyl itaconate, diallyl fumarate, and diallyl maleate; polyallyl ethers of sucrose having from 2 to 8 allyl groups per molecule, polyallyl ethers of pentaerythritol such as pentaerythritol diallyl ether, pentaerythritol triallyl ether, and pentaerythritol tetraallyl ether, and combinations thereof; polyallyl ethers of trimethylolpropane such as trimethylolpropane diallyl ether, trimethylolpropane triallyl ether, and combinations thereof. Other suitable polyunsaturated compounds include divinyl glycol, divinyl benzene, and methylenebisacrylamide.

When homopolymers prepared from the monoethylenically unsaturated $C_3$-$C_6$ carboxylic acid group containing monomer or anhydride are contemplated, the amount of carboxylic monomer residue in the polymer ranges from about 95 to about 99.99 wt. %, and the amount of optional crosslinking monomer residue ranges from about 0.01 to about 5 wt. % based on the total weight of monomers utilized to prepare the polymer. In another aspect, the amount of optional crosslinking monomer residues in the polymer can range from about 0.05 to about 4 wt. %, from about 0.1 to about 3.5 wt. %, and from about 1 to about 2.5 wt. % with the balance made up by the monoethylenically unsaturated $C_3$-$C_6$ carboxylic acid group containing monomer residues to total 100 wt. %.

When copolymers prepared from the monoethylenically unsaturated $C_3$-$C_6$ carboxylic acid group containing monomer or anhydride are contemplated, the amount of carboxylic group containing monomer residues in the polymer can range from about 60 to about 99 wt. %, the amount of comonomer residues of formula (I) and/or formula (II) can range from about 1 to about 40 wt. %, and the amount of optional crosslinking monomer residues range from about 0.01 to about 5 wt. %, based on the total weight of monomer residues in the polymer. In another aspect, the amount of optional crosslinking monomer residues can range from about 0.05 to about 4 wt. %, or from about 0.1 to about 3.5 wt. %, or from about 1 to about 2.5 wt. % with the balance made up by the monoethylenically unsaturated carboxylic acid containing monomer residues and the amount of comonomer residues of formula (I) and/or formula (II) to total 100 wt. %.

The synthetically derived anionic polymer can be prepared using polymerization techniques that are well-known to a person skilled in the art. These known polymerization techniques include solution polymerization, precipitation polymerization, aqueous emulsion polymerization, and the like. Polymers prepared by solution and precipitation polymerization are generally isolated from the polymerization medium in powdered from, while polymers prepared by aqueous emulsion techniques are obtained in liquid latex form.

The foregoing synthetically derived anionic polymers may further be classified by their INCI names such as, for example, Carbomer, Acrylates/C10-30 Alkyl Acrylate Crosspolymer, Acrylates Copolymer, Acrylates Crosspolymer-4, Sodium Polyacrylate and Acrylates/Vinyl Neodecanoate Crosspolymer.

Commercially available Carbomer is marketed under the Carbopol™ trade name having product designations 934, 940, 941, 980, 981, 2984, 5984, ETD 2050, Ultrez 10 and Ultrez 30 by Lubrizol Advanced Materials, Inc. Commercially available Acrylates/C10-30 Alkyl Acrylate Crosspolymer is marketed under the Carbopol™ trade name having product designations 1342, 1382, ETD 2050, SC-500, Ultrez 20, and Ultrez 21, as well as under the Pemulen trade name product designations TR-1, TR-2 and EZ-4U from Lubrizol Advanced Materials, Inc. Commercially available Acrylates Copolymer is marketed under the Carbopol™ trade name having the product designations Aqua SF-1 and Aqua SF-3. Commercially available Acrylates Crosspolymer-4 is marketed under the Carbopol™ trade name having product designation Aqua SF-2. Commercially available Sodium Polyacrylate is marketed by Lubrizol Advanced Materials under the Carbosperse™ trade name under product designations K-732, K-739. K-759, K-702, K-7028, K-7058D, K-7058N and K-7600N. Commercially available Acrylates/Vinyl Neodecanoate Crosspolymer is available from Dow Chemical Company under the Aculyn™ 38 trade name.

In one aspect, the personal care deposition compositions may contain a polymer selected from a naturally derived anionic polymer and/or a derivatized naturally derived anionic polymer. Exemplary naturally derived and derivatized naturally derived anionic polymers include but are not limited to cellulose gum, xanthan gum, dehydroxanthan gum, carboxymethylcellulose, acacia gum, gum Arabic, alginic acid, gum karya, gum tragacanth, diutan gum, carrageenan gum, gellan gum, and mixtures thereof.

In one aspect, the deposition compositions of the present technology comprise from about 0.01 to about 2 wt. %, or from about 0.05 to about 0.5 wt. %, or from about 0.1 to about 0.3 wt. % of the at least one anionic polymer, based on the total weight of the composition. The anionic polymer may be synthetic, natural or a combination of synthetic and natural.

In one aspect, when a naturally derived anionic polymer(s) is utilized in combination with the anionic polymer(s) in the deposition composition, the composition comprises from about 0.01 to about 1 wt. %, or from about 0.5 to about 0.5 wt. %, or from about 0.1 to about 0.3 wt. % of the naturally derived anionic polymer, based on the total weight of the composition.

In one aspect, the weight ratio of ampholytic polymer to anionic polymer (including the natural anionic polymer if present) is from about 10:1 to about 1:1, or from about 7:1 to about 2:1, or from about 5:1 to about 3:1.

Lipophilic Materials

Lipophilic material as used herein means a lipophilic active typically delivered to an external surface of the human body to enhance or improve a characteristic of the surface. The lipophilic material includes any water insoluble, oil miscible, or lipophilic substance which benefits the keratinous substrate. The personal care deposition compositions of the present technology may comprise a one lipophilic material or a mixture of two or more lipophilic materials. The at least one lipophilic material suitable for use in the present technology is selected from essential oils, fragrance oils, ester oils, glyceride oils, plant oils, fatty alcohols, silicone oils, hydrocarbon oils, petrolatum, plant waxes, plant butters, water insoluble or slightly soluble organic sunscreens, micronized sunscreens, plant extracts, hydrophobically modified pigments (e.g., Natural Orange 4 (CI75120), D&C Violet 2 (CI60725), D&C Red 17 (CI26100), D&C Green 6 (CI61565), D&C Red 6 or Red 7(CI15850), and Quinoline Yellow SS (47000)), hydrophobic vitamin or vitamin complexes, antioxidants, antifungal agents (e.g., zinc pyrithione), anti-inflammatory actives, antimicrobials, antiperspirant actives, deodorant actives, skin health actives, and mixtures thereof.

In one aspect, exemplary essential oils include, but are not limited to, oil of *eucalyptus*, oil of hybrid lavender, oil of lavender, oil of vetiver, oil of *Litsea cubeba*, oil of lemon and lime (limonene), cinnamaldehyde, oil of cinnamon (bark), oil of cinnamon (leaf), oil of sandalwood, oil of rosemary, oil of chamomile, oil of savory, oil of nutmeg, oil of cinnamon, oil of hyssop, oil of caraway, oil of orange, oil of tea tree, oil of geraniol, oil of eugenol, oil of carvacrol, oil of prickly juniper, and oil of bergamot.

Fragrance oils, unlike the naturally derived essential oils, are synthetically manufactured scents. Exemplary fragrance oils are anethol, methyl heptine carbonate, ethyl aceto acetate, para cymene, nerol, decyl aldehyde, para cresol, methyl phenyl carbinyl acetate, ionone alpha, ionone beta, undecylenic aldehyde, undecyl aldehyde, 2,6-nonadienal, nonyl aldehyde, octyl aldehyde, phenyl acetaldehyde, anisic aldehyde, benzyl acetone, ethyl-2-methyl butyrate, damascenone, damascone alpha, damascone beta, for acetate, frutene, fructone, herbavert, methyl isobutenyl tetrahydropyran, isopropyl quinoline, 2,6-nonadien-1-ol, 2-methoxy-3-(2-methylpropyl)-pyrazine, methyl octine carbonate, cyclogalbanate, gamma nonalactone, cis 1,3-oxathiane-2-methyl-4-propyl, benzaldehyde, benzyl acetate, camphor, carvone, borneol, bornyl acetate, decyl alcohol, eucalyptol, linalool, hexyl acetate, iso-amyl acetate, thymol, carvacrol, limonene, menthol, iso-amyl alcohol, phenyl ethyl alcohol, alpha pinene, alpha terpineol, citronellol, alpha thujone, benzyl alcohol, beta gamma hexenol, dimethyl benzyl carbinol, phenyl ethyl dimethyl carbinol, adoxal, allyl cyclohexane propionate, beta pinene, citral, citronellyl acetate, citronellal nitrile, dihydro myrcenol, geraniol, geranyl acetate, geranyl nitrile, hydroquinone dimethyl ether, hydroxycitronellal, linalyl acetate, phenyl acetaidehyde dimethyl acetal, phenyl propyl alcohol, prenyl acetate, tetrahydrolinalool, verdox, and cis-3-hexenyl acetate, ethyl methyl phenyl glycidate, ethyl vanillin, heliotropin, Indol, methyl anthranilate, vanillin, amyl salicylate, coumarin, ambrox, bacdanol, benzyl salicylate, butyl anthranilate, cetalox, ebanol, cis-3-hexenyl salicylate, lilial, gamma undecalactone, gamma dodecalactone, gamma decalactone, calone, cymal, dihydro iso jasmonate, iso eugenol, lyral, methyl beta naphthyl ketone, beta naphthol methyl ether, para hydroxy I phenyl butanone, 8-cyclohexadecen-1-one, oxocyclohexadecen-2-one/habanolide, florhydral, intreleven aldehyde eugenol, amyl cinnamic aldehyde, hexyl cinnamic aldehyde, hexyl salicylate, methyl dihydro jasmonate, sandalore, veloutone, undecavertol, exaltolide/cyclopentadecanolide, zingerone, methyl cedrylone, sandela, dimethyl benzyl carbinyl butyrate, dimethyl benzyl carbinyl isobutyrate, triethyl citrate, cashmeran, phenoxy ethyl isobutyrate, iso eugenol acetate, helional, Iso E Super™, ionone gamma methyl, pentalide, galaxolide, phenoxy ethyl propionate, and mixtures thereof.

The ester oils are characterized by having at least 12 carbon atoms and include esters with hydrocarbon chains derived from fatty acids or alcohols, e.g., mono-esters, polyhydric alcohol esters, and di- and tri-carboxylic acid esters. The hydrocarbyl radicals of the fatty esters hereof can also include or have covalently bonded thereto other compatible functionalities, such as amides and alkoxy moieties (e.g., ethoxy or ether linkages).

The monocarboxylic acid esters include esters of alcohols and/or acids of the formula R'COOR wherein the alkyl or alkenyl radicals and the sum of carbon atoms in R' and R is at least 10, or at least 20.

Ester oils include, for example, alkyl and alkenyl esters of fatty acids having aliphatic chains having from about 10 to about 22 carbon atoms, and alkyl and alkenyl fatty alcohol carboxylic acid esters having an alkyl and/or alkenyl alcohol derived aliphatic chain with about 10 to about 22 carbon atoms, and combinations thereof. Examples include lauryl lactate, myristyl lactate, cetyl lactate, hexyl laurate, isohexyl laurate, myristyl myristate, cetyl myristate, stearyl myristate, isostearyl myristate, oleyl myristate, behenyl myristate, erucyl myristate, isopropyl palmitate, isohexyl palmitate, myristyl palmitate, cetyl palmitate, stearyl palmitate, isostearyl palmitate, oleyl palmitate, behenyl palmitate, erucyl palmitate, isopropyl isostearate, decyl stearate, myristyl stearate, myristyl isostearate, cetyl stearate, cetyl isostearate, stearyl stearate, stearyl isostearate, isostearyl stearate, isostearyl isostearate, oleyl stearate, oleyl isostearate, behenyl stearate, behenyl isostearate, erucyl stearate, erucyl isostearate, decyl oleate, isodecyl oleate, myristyl oleate, cetyl oleate, stearyl oleate, isostearyl oleate, oleyl oleate, behenyl oleate, erucyl oleate, myristyl behenate, cetyl behenate, stearyl behenate, isostearyl behenate, oleyl behenate, behenyl behenate, erucyl behenate, myristyl erucate, cetyl erucate, oleyl erucate, and erucyl erucate.

Di- and tri-alkyl and alkenyl esters of carboxylic acids can also be used. These include, for example, esters of $C_4$-$C_8$ dicarboxylic acids such as $C_1$-$C_{22}$ esters of succinic acid, glutaric acid, adipic acid, hexanoic acid, heptanoic acid, and octanoic acid. Representative examples include isocetyl stearyl stearate, diisopropyl adipate, diisohexyl adipate, dihexyldecyl adipate, diisopropyl sebacate and tristearyl citrate. Polyhydric alcohol esters include alkylene glycol esters (di-fatty acid esters), ethylene glycol (mono- and di-fatty acid esters), polyethylene glycol (mono and di-fatty acid esters), propylene glycol (mono- and di-fatty acid esters), polypropylene glycol mono oleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, polyoxyethylene sorbitan fatty acid esters are satisfactory polyhydric alcohol esters for use as ester oils.

Representative glyceride oils include, but are not limited to, di- and tri-esters of glycerol and fatty acids having 6 to 22, or 8 to 18, or 10 to 16 carbon atoms, and mixtures thereof. In one aspect, the fatty acids utilized to prepare the glyceride oils can be saturated or unsaturated, linear or branched, substituted or unsubstituted. Exemplary glyceride oils include, but are not limited to, acetoglyceryl, glyceryl triisooctanoate, glyceryl triisostearate, glyceryl triisopalmitate, glyceryl tri(caprylate.caprate), glyceryl monostearate, glyceryl di-2-heptylundecanoate, glyceryl trimyristate, diglyceryl myristate isostearate, caprylic/capric triglyceride, and mixtures thereof.

In one aspect, plant oils include olive oil, sunflower oil, soya oil, groundnut oil, peanut oil, rapeseed oil, sweet almond oil, jojoba oil, borage oil, palm oil, coconut oil, castor oil, hydrogenated castor oil, barley oil, walnut oil, wheatgerm oil, grapeseed oil, evening primrose oil, macadamia nut oil, babassu oil, carrot oil, palm kernel oil, shea butter oil, sesame oil, peach stone oil, corn oil, karite butter, apricot oil, cottonseed oil, alfalfa oil, poppy oil, pumpkin oil, marrow oil, grapefruit seed oil, avocado oil, hazelnut oil, blackcurrant seed oil, millet oil, barley oil, rye oil, *quinoa* oil, olive oil, rye oil, safflower oil, candlenut oil, *passiflora* oil, passion flower oil, musk rose oil, *camellia* oil, camelina oil, pine oil, tamanu oil, and mixtures thereof.

In one aspect, the fatty alcohols are selected from linear and branched, saturated and unsaturated $C_{12}$ to $C_{30}$ fatty alcohols. Non-limiting examples of fatty alcohols are lauryl alcohol, myristyl alcohol, cetyl alcohol, isocetyl alcohol, stearyl alcohol, isostearyl alcohol, cetearyl alcohol, palmitoleyl alcohol, elaidyl alcohol, sterol, oleyl alcohol, linoleyl alcohol, elaidolinoleyl alcohol, linolenyl alcohol, ricinoleyl alcohol, arachidyl alcohol, icocenyl alcohol, behenyl alcohol, erucyl alcohol, lignoceryl alcohol, ceryl alcohol, montanyl alcohol, myricyl alcohol, tridecyl alcohol, and mixtures thereof. Fatty alcohols are widely available and can be obtained through the hydrogenation of esterified vegetable and animal oils and fats.

Silicone oils are synthetic polymeric compounds in which the silicon atoms are bonded together via oxygen atoms. In one aspect, the silicone oil is non-volatile and insoluble in the aqueous phase of the present composition. By non-volatile is meant that the silicone has a very low vapor pressure at ambient temperature conditions (e.g., less than 2 mm Hg at 20° C.). The non-volatile silicone conditioning agent has a boiling point above about 250° C., or above about 260° C., or above about 275° C. in a further aspect. Background information on silicones including sections discussing silicone oils, gums, and resins, as well as their manufacture, are found in Encyclopedia of Polymer Science and Engineering, vol. 15, 2d ed., pp 204-308, John Wiley & Sons, Inc. (1989).

Suitable silicone oils include, but are not limited to, higher alkoxy-modified silicones and higher fatty acid-modified silicones such as dimethylpolysiloxane, methylphenylpolysiloxane, methylhydrogenpolysiloxane, octamethylcyclotetrasiloxane, decamethylcyclopentasiloxane, dodecamethylcyclohexasiloxane, tetramethyltetrahydrogencyclotetrasiloxane, and stearoxysilicone as well as fluorine-modified silicones, amino-modified silicones, alkyl-modified silicones, and mixtures thereof.

Hydrocarbon oils include volatile hydrocarbon oils, non-volatile hydrocarbon oils, and mixtures thereof. Suitable volatile hydrocarbon oils include linear or branched, optionally cyclic, $C_5$-$C_{20}$ lower alkanes. Examples include, but are not limited to pentane, hexane, heptane, decane, undecane, dodecane, tridecane, tetradecane and $C_8$-$C_{18}$ isoparaffins, for example, isodecane, isododecane and isohexadecane.

In one aspect, the hydrocarbon oils are paraffinic hydrocarbons including $C_{12}$ and $C_{16}$ isoparaffins. Such isoparaffinic hydrocarbons are available from ExxonMobil under the Isopars™ trade name, and from the Permethyl Corporation marketed under the Permethyl™ trade name. Exemplary $C_{12}$ isoparaffins (isododecane) are commercially available from Permethyl Corporation under the trade name Permethyl 99A. A $C_{16}$ isoparaffin (isohexadecane) that is commercially available under the Permethyl 101A tradename, is also suitable. Other examples of hydrocarbon oils include polydecene, polyisobutene, petrolatum and mineral oil. Mixtures of hydrocarbon oils are contemplated.

Plant waxes include, but are not limited to, olive tree wax, rice wax, carnauba wax, fruit waxes, hydrogenated jojoba wax or the absolute waxes of flowers such as the essential wax of blackcurrant flower marketed by Huiles Bertin, lanolin, beeswaxes, modified beeswaxes, marine waxes, and mixtures thereof.

Plant butters are butter-like compositions made with plant-based oils. Such butters are generally characterized by their hydrocarbon chain length as taught in U.S. Pat. No. 5,554,408. Non-limiting plant butters useful in the present compositions include, almond butter, hemp seed butter, shea butter, cocoa butter, coconut butter, aloe butter, jojoba butter, lavender butter, lemon butter, lime butter orange peel butter, tangerine butter, soy butter, tucuma butter, turmeric butter, ucuuba butter, rose hip butter, argan butter, *arnica* butter, macadamia butter, avocado butter, mango butter, bacuri butter, chamomile butter, chia butter, carrot butter, green tea butter, olive butter, moringa butter, oat butter, prickly pear butter, pumpkin seed butter, kokum butter, murumuru butter, cupuacu butter, babassu butter, and mixtures thereof.

Mixtures of one or more of the foregoing oily materials are contemplated within the scope of the present technology.

Aqueous Medium

The aqueous phase is primarily water, usually deionized, distilled or tap water (nominal hardness). In one aspect, the deposition compositions of the present technology comprise from about 30 to about 95 wt. %, or from about 50 to about 90 wt. %, or from about 70 to about 85 wt. % water.

Surfactants

In one aspect of the present technology, the deposition compositions may contain a surfactant selected from at least one anionic surfactant, at least one cationic surfactant, at least one amphoteric and/or a zwitterionic surfactant, at least one nonionic surfactant, and mixtures thereof.

Anionic

In one aspect, the deposition compositions of the present technology may contain an anionic surfactant. Suitable anionic surfactants include but are not limited to alkyl sulfates, alkyl ether sulfates, alkyl sulfonates, alkaryl sulfonates, α-olefin-sulfonates, alkylamide sulfonates, alkarylpolyether sulphates, alkylamidoether sulfates, alkyl monoglyceryl ether sulfates, alkyl monoglyceride sulfates, alkyl monoglyceride sulfonates, alkyl succinates, alkyl sulfosuccinates, alkyl ether sulfosuccinates, alkyl sulfosuccinamates, alkyl am idosulfosuccinates; alkyl sulfoacetates, alkyl phosphates, alkyl ether phosphates, alkyl ether carboxylates, alkyl am idoethercarboxylates, acyl lactylates, alkyl isethionates, acyl isethionates, carboxylate salts and amino acid derived surfactants such as N-alkyl amino acids, N-acyl amino acids, as well as alkyl peptides. In addition, fatty acid soaps can be employed. Mixtures of the foregoing anionic surfactants are also useful.

In one aspect, the cation moiety of the forgoing surfactants is selected from sodium, potassium, magnesium, ammonium, and alkanolammonium ions such as monoethanolammonium, diethanolammonium triethanolammonium ions, as well as monoisopropylammonium, diisopropylammonium and triisopropylammonium ions. In one embodiment, the alkyl and acyl groups of the foregoing surfactants contain from about 6 to about 24 carbon atoms in one aspect, from 8 to 22 carbon atoms in another aspect and from about 12 to 18 carbon atoms in a further aspect and may be unsaturated. The aryl groups in the surfactants are selected from phenyl or benzyl. The ether containing surfactants set forth above can contain from 1 to 10 ethylene oxide and/or propylene oxide units per surfactant molecule in one aspect, and from 1 to 3 ethylene oxide units per surfactant molecule in another aspect.

Examples of suitable anionic surfactants include the sodium, potassium, lithium, magnesium, and ammonium salts of laureth sulfate, trideceth sulfate, myreth sulfate, $C_{12}$-$C_{13}$ pareth sulfate, $C_{12}$-$C_{14}$ pareth sulfate, and $C_{12}$-$C_{15}$ pareth sulfate, ethoxylated with 1, 2, and 3 moles of ethylene oxide; the sodium potassium, lithium, magnesium, ammonium, and triethanolammonium salts of lauryl sulfate, coco sulfate, tridecyl sulfate, myristyl sulfate, cetyl sulfate, cetearyl sulfate, stearyl sulfate, oleyl sulfate, and tallow sulfate, disodium lauryl sulfosuccinate, disodium laureth sulfosuccinate, sodium cocoyl isethionate, sodium lauroyl isethionate, sodium lauroyl methyl isethionate, sodium $C_{12}$-$C_{14}$ olefin sulfonate, sodium laureth-6 carboxylate, sodium dodecylbenzene sulfonate, triethanolamine monolauryl phosphate, and fatty acid soaps, including the sodium, potassium, ammonium, and triethanolamine salts of a saturated and unsaturated fatty acids containing from about 8 to about 22 carbon atoms.

In one aspect, the amino acid surfactants are selected from a N-acyl amino acid of the formula:

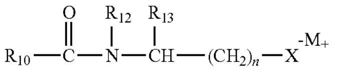

wherein $R_{10}$ is a saturated or unsaturated, straight or branched alkyl chain containing 7 to 17 carbon atoms, $R_{12}$ is H or a methyl group, $R_{13}$ is H, $COOM^-M^+$, $CH_2COO^-M^+$ or COOH, n is 0 to 2, X is $COO^-$ or $SO_3^-$ and M independently represents H, sodium, potassium, ammonium or triethanolammonium.

In one aspect, the N-acyl amino acid surfactants represented by the formula immediately above are derived from taurates, glutamates, alanine, alaninates, sacosinates, aspartates, glycinates, and mixtures thereof.

Representative taurate surfactants conform to the formula:

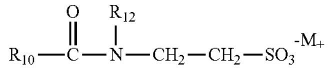

wherein $R_{10}$ is a saturated or unsaturated, straight or branched alkyl chain containing 7 to 17 carbon atoms in one aspect and 9 to 13 carbon atoms in another aspect, $R_{12}$ is H or methyl, and M is H, sodium, potassium, ammonium or triethanolammonium.

Non-limiting examples of taurate surfactants are potassium cocoyl taurate, potassium methyl cocoyl taurate, sodium caproyl methyl taurate, sodium cocoyl taurate, sodium lauroyl taurate, sodium methyl cocoyl taurate, sodium methyl lauroyl taurate, sodium methyl myristoyl taurate, sodium methyl oleoyl taurate, sodium methyl palmitoyl taurate, sodium methyl stearoyl taurate, and mixtures thereof.

Representative glutamate surfactants conform to the formula:

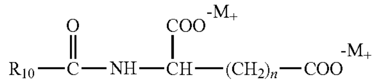

wherein $R_{10}$ is a saturated or unsaturated, straight or branched alkyl chain containing 7 to 17 carbon atoms in one aspect and 9 to 13 carbon atoms in another aspect, n is 0 to 2, and M independently is H, sodium, potassium, ammonium or triethanolammonium.

Non-limiting examples of glutamate surfactants are di-potassium capryloyl glutamate, di-potassium undecylenoyl glutamate, di-sodium capryloyl glutamate, di-sodium cocoyl glutamate, di-sodium lauroyl glutamate, di-sodium stearoyl glutamate, di-sodium undecylenoyl glutamate, potassium capryloyl glutamate, potassium cocoyl glutamate, potassium lauroyl glutamate, potassium myristoyl glutamate, potassium stearoyl glutamate, potassium undecylenoyl glutamate, sodium capryloyl glutamate, sodium cocoyl glutamate, sodium lauroyl glutamate, sodium myristoyl glutamate, sodium olivoyl glutamate, sodium palmitoyl glutamate, sodium stearoyl glutamate, sodium undecylenoyl glutamate, and mixtures thereof.

Representative alanine and alaninate surfactants conform to the formula:

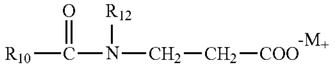

wherein $R_{10}$ is a saturated or unsaturated, straight or branched alkyl chain containing 7 to 17 carbon atoms in one aspect and 9 to 13 carbon atoms in another aspect, $R_{12}$ is H or methyl, and M is H, sodium, potassium, ammonium or triethanolammonium.

Non-limiting examples of alanine and alaninate surfactants are cocoyl methyl β-alanine, lauroyl β-alanine, lauroyl methyl β-alanine, myristoyl β-alanine, potassium lauroyl methyl β-alanine, sodium cocoyl alaninate, sodium cocoyl methyl β-alanine, sodium myristoyl methyl β-alanine, and mixtures thereof.

Representative glycinate surfactants conform to the formula:

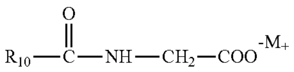

wherein $R_{10}$ is a saturated or unsaturated, straight or branched alkyl chain containing 7 to 17 carbon atoms in one aspect and 9 to 13 carbon atoms in another aspect, and M is H, sodium, potassium, ammonium or triethanolammonium.

Non-limiting examples of glycinate surfactants are sodium palmitoyl glycinate, sodium lauroyl glycinate, sodium cocoyl glycinate, sodium myristoyl glycinate, potassium lauroyl glycinate, potassium cocoyl glycinate, sodium stearoyl glycinate, and mixtures thereof.

Representative sarcosinate surfactants conform to the formula:

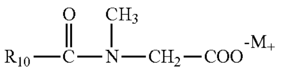

wherein $R_{10}$ is a saturated or unsaturated, straight or branched alkyl chain containing 7 to 17 carbon atoms in one aspect and 9 to 13 carbon atoms in another aspect, and M is H, sodium, potassium, ammonium or triethanolamine.

Non-limiting examples of sarcosinate surfactants are potassium lauroyl sarcosinate, potassium cocoyl sarcosinate, sodium cocoyl sarcosinate, sodium lauroyl sarcosinate, sodium myristoyl sarcosinate, sodium palmitoyl sarcosinate, and mixtures thereof.

Representative aspartate surfactants conform to the formula:

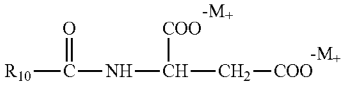

wherein $R_{10}$ is a saturated or unsaturated, straight or branched alkyl chain containing 7 to 17 carbon atoms in one aspect and 9 to 13 carbon atoms in another aspect, and M independently is H, sodium, potassium, ammonium or triethanolammonium.

Non-limiting examples of aspartate surfactants are sodium lauroyl aspartate, sodium myristoyl aspartate, sodium cocoyl aspartate, sodium caproyl aspartate, di-sodium lauroyl aspartate, di-sodium myristoyl aspartate, di-sodium cocoyl aspartate, di-sodium caproyl aspartate, potassium lauroyl aspartate, potassium myristoyl aspartate, potassium cocoyl aspartate, potassium caproyl aspartate, di-potassium lauroyl aspartate, di-potassium myristoyl aspartate, di-potassium cocoyl aspartate, di-potassium caproyl aspartate, and mixtures thereof.

In one aspect of the disclosed technology, the deposition composition may comprise at least one the fatty acid soap containing from about 8 to about 22 carbon atoms. In another aspect, the deposition composition contains at least one fatty acid salt soap containing from about 10 to about 18 carbon atoms. In a further aspect of the disclosed technology the cleansing composition contains at least one fatty acid soap containing from about 12 to about 16 carbon atoms. The fatty acids utilized in the soaps can be saturated and unsaturated and can be derived from synthetic sources, as well as from the hydrolysis of fats and natural oils. Exemplary saturated fatty acids include but are not limited to octanoic, decanoic, lauric, myristic, pentadecanoic, palmitic, margaric, steric, isostearic, nonadecanoic, arachidic, behenic, and the like, and mixtures thereof. Exemplary unsaturated fatty acids include but are not limited to myristoleic, palmitoleic, oleic, linoleic, linolenic, and the like, and mixtures thereof. The fatty acids can be derived from animal fat such as tallow, lard, poultry fat or from vegetable sources such as coconut oil, red oil, palm kernel oil, palm oil, cottonseed oil, linseed oil, sunflower seed oil, olive oil, soybean oil, peanut oil, corn oil, safflower oil, sesame oil, rapeseed oil, canola oil, and mixtures thereof.

Cationic

In one aspect of the present technology, suitable cationic surfactants include but are not limited to alkylamines, amidoamines, alkyl imidazolines, ethoxylated amines, quaternary compounds, and quaternized esters. In addition, alkylamine oxides can function as a cationic surfactant at a lower pH values.

Non-limiting examples of alkylamines and salts thereof include dimethyl cocamine, dimethyl palmitamine, dioctylamine, dimethyl stearamine, dimethyl soyamine, soyamine, myristyl amine, tridecyl amine, ethyl stearylamine, N-tallowpropane diamine, ethoxylated stearylamine, dihydroxy ethyl stearylamine, arachidylbehenylamine, dimethyl lauramine, stearylamine hydrochloride, soyamine chloride, stearylamine formate, N-tallowpropane diamine dichloride, and amodimethicone (INCI name for a silicone polymer and blocked with amino functional groups, such as aminoethylamino propylsiloxane).

Non-limiting examples of amidoamines and salts thereof include stearamido propyl dimethyl amine, stearamidopropyl dimethylamine citrate, palmitamidopropyl diethylamine, and cocamidopropyl dimethylamine lactate.

Non-limiting examples of alkyl imidazoline surfactants include alkyl hydroxyethyl imidazoline, such as stearyl hydroxyethyl imidazoline, coco hydroxyethyl imidazoline, ethyl hydroxymethyl oleyl oxazoline, and the like.

Non-limiting examples of ethyoxylated amines include PEG-cocopolyamine, PEG-15 tallow amine, quaternium-52, and the like.

Exemplary quaternary ammonium surfactants include, but are not limited to cetyl trimethylammonium chloride, cetylpyridinium chloride, dicetyl dimethyl ammonium chloride, dihexadecyl dimethyl ammonium chloride, stearyl dimethyl benzyl ammonium chloride, dioctadecyl dimethyl ammonium chloride, dieicosyl dimethyl ammonium chloride, didocosyl dimethyl ammonium chloride, dihexadecyl dimethyl ammonium chloride, dihexadecyl dimethyl ammonium acetate, behenyl trimethyl ammonium chloride, benzalkonium chloride, benzethonium chloride, and di(cocoalkyl) dimethyl ammonium chloride, ditallowdimethyl ammonium chloride, di(hydrogenated tallow) dimethyl ammonium chloride, di(hydrogenated tallow) dimethyl ammonium acetate, ditallowdimethyl ammonium methyl sulfate, ditallow dipropyl ammonium phosphate, and ditallow dimethyl ammonium nitrate.

At low pH values, alkylamine oxides can protonate and behave similarly to N-alkyl amines.

Amphoteric/Zwitterionic

In one aspect of the present technology, suitable amphoteric surfactants include but are not limited to alkyl betaines, e.g., lauryl betaine; alkylamido betaines, e.g., cocamidopropyl betaine and cocohexadecyl dimethylbetaine; alkylamido sultaines, e.g., cocamidopropyl hydroxysultaine; (monoand di-) amphocarboxylates, e.g., sodium cocoamphoacetate, sodium lauroamphoacetate, sodium capryloamphoacetate, disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, and disodium capryloamphodipropionate; amine oxides, e.g., dimethyldodecylamine oxide, oleyldi(2-hydroxyethyl) amine oxide, dimethyltetradecylamine oxide, di(2-hydroxyethyl)-tetradecylamine oxide, dimethylhexadecylamine oxide, behenamine oxide, cocamine oxide, decyltetradecylamine oxide, dihydroxyethyl $C_{12-15}$ alkoxypropylamine oxide, dihydroxyethyl cocamine oxide, dihydroxyethyl lauramine oxide, dihydroxyethyl stearamine oxide, dihydroxyethyl tallowamine oxide, hydrogenated palm kernel amine oxide, hydrogenated tallowamine oxide, hydroxyethyl hydroxypropyl $C_{12}$-$C_{15}$ alkoxypropylamine oxide, lauramine oxide, myristamine oxide, cetylamine oxide, oleamidopropylamine oxide, oleamine oxide, palmitamine oxide, PEG-3 lauramine oxide, dimethyl lauramine oxide, potassium trisphosphonomethylamine oxide, soyamidopropylamine oxide, cocamidopropylamine oxide, stearamine oxide, tallowamine oxide, and mixtures thereof, and mixtures thereof.

The foregoing amphoteric surfactants (i.e., the betaines and sultaines are disclosed without a counter ion, as one of ordinary skill in the art will recognize that the under the pH conditions of the compositions containing the amphoteric surfactants, these surfactants are either electrically neutral by virtue of having balancing positive and negative charges, or they contain counter ions such as alkali metal, alkaline earth or ammonium ions as a charge balancing moiety.

Nonionic

In one aspect, the nonionic surfactant is an alcohol alkoxylate derived from a saturated or unsaturated fatty alcohol containing 8 to 18 carbon atoms, and the number of alkylene oxide groups present in the alcohol range from about 3 to about 12. The alkylene oxide moiety is selected from ethylene oxide, propylene oxide and combinations thereof. In another aspect, the alcohol alkoxylate is derived from a fatty alcohol containing 8 to 15 carbon atoms and contains from 5 to 10 alkoxy groups (e.g. ethylene oxide, propylene oxide, and combinations thereof). Exemplary nonionic fatty alcohol alkoxylate surfactants in which the alcohol residue contains 12 to 15 carbon atoms and contain about 7 ethylene oxide groups are available under the Tomadol® (e.g., product designation 25-7) and Neodol® (e.g., product designation 25-7) trade names from Tomah Products, Inc. and Shell Chemicals, respectively.

An exemplary nonionic alcohol alkoxylated surfactant derived from an unsaturated fatty alcohol and containing about 10 ethylene oxide groups is available from Lubrizol Advanced Materials, Inc. under the trade Chemonic™ oleth-10 ethoxylated alcohol.

Another commercially available alcohol alkoxylate surfactant is sold under the Plurafac® trade name from BASF. The Plurafac surfactants are reaction products of a higher linear alcohol and a mixture of ethylene and propylene oxides, containing a mixed chain of ethylene oxide and propylene oxide, terminated by a hydroxyl group. Examples include $C_{13}$ to $C_{15}$ fatty alcohols condensed with 6 moles ethylene oxide and 3 moles propylene oxide, $C_{13}$ to $C_{15}$ fatty alcohols condensed with 7 moles propylene oxide and 4 moles ethylene oxide, and $C_{13}$ to $C_{15}$ fatty alcohols condensed with 5 moles propylene oxide and 10 moles ethylene oxide.

Another commercially suitable nonionic surfactant is available from Shell Chemicals under the Dobanol™ trade name (product designations 91-5 and 25-7). Product designation 91-5 is an ethoxylated $C_9$ to $C_{11}$ fatty alcohol with an average of 5 moles ethylene oxide and product designation 25-7 is an ethoxylated $C_{12}$ to $C_{15}$ fatty alcohol with an average of 7 moles ethylene oxide per mole of fatty alcohol.

Another commercially suitable nonionic surfactant is available from Shell Chemicals under the Dobanol™ trade name (product designations 91-5 and 25-7). Product designation 91-5 is an ethoxylated $C_9$ to $C_{11}$ fatty alcohol with an average of 5 moles ethylene oxide and product designation 25-7 is an ethoxylated $C_{12}$ to $C_{15}$ fatty alcohol with an average of 7 moles ethylene oxide per mole of fatty alcohol.

Other surfactants which can be utilized in the cleansing compositions of the present technology are set forth in more detail in WO 99/21530, U.S. Pat. Nos. 3,929,678, 4,565,647, 5,456,849, 5,720,964, 5,858,948, and 7,115,550, which are herein incorporated by reference. Additionally, suitable surfactants are described in McCutcheon's Emulsifiers and Detergents (North American and International Editions, by Schwartz, Perry and Berch) which is hereby fully incorporated by reference.

In one aspect, the surfactant(s) utilized in the deposition composition of the present technology can be employed in amounts typically utilized in personal care cleansing compositions. In one aspect, the at least one surfactant is utilized in an amount ranging from about 5 to about 30 wt. %, or from about 7 to about 25 wt. %, or from about 9 to about 20 wt. %, based on the total weight of the deposition composition.

In one aspect, the surfactant is selected from a combination of an anionic surfactant and an amphoteric surfactant. In one aspect, the weight ratio of anionic surfactant to amphoteric surfactant (based on the active material) is from about 10:1 to about 2:1 in one aspect, and 9:1, 8:1, 7:1 6:1, 5:1, 4.5:1, 4:1, or 3:1 in another aspect.

In one aspect the pH of the personal care deposition composition can range from about 3.5 to about 10, or from about 4 to about 7, or from about 4.8 to about 6. The pH of the deposition compositions of the present invention can be adjusted with any combination of acidic and/or basic pH adjusting agent known to the art. Acidic pH adjusting agents include organic acids and inorganic acids, for example, acetic acid, citric acid, tartaric acid, alpha-hydroxy acids, beta-hydroxy acids, salicylic acid, lactic acid, glycolic acid, and natural fruit acids, or inorganic acids, for example, hydrochloric acid, nitric acid, sulfuric acid, sulfamic acid, phosphoric acid, and combinations thereof. Basic pH adjusting agents include inorganic and organic bases. Examples of inorganic bases include but are not limited to the alkali metal hydroxides (especially sodium, potassium, and ammonium), and alkali metal salts of inorganic acids, such as sodium borate (borax), sodium phosphate, sodium pyrophosphate, and the like; and mixtures thereof. Examples of organic bases include but are not limited to triethanolamine (TEA), diisopropanolamine, triisopropanolamine, aminomethyl propanol, dodecylamine, cocamine, oleamine, morpholine, triamylamine, triethylamine, tetrakis(hydroxypropyl)ethylenediamine, L-arginine, aminomethyl propanol, tromethamine (2-amino 2-hydroxymethyl-1,3-propanediol), and PEG-15 cocamine, and mixtures thereof.

In one aspect, buffering agents can be used in the compositions of the invention. Suitable buffering agents include, but are not limited to, alkali or alkali earth metal carbonates, phosphates, bicarbonates, citrates, borates, acetates, acid anhydrides, succinates, and the like, such as sodium phosphate, sodium citrate, sodium acetate, sodium bicarbonate, sodium carbonate, and mixtures thereof.

The deposition compositions of the present technology may contain one or more of a wide variety of optional components well-known to those skilled in the art so long as their addition does not interfere with the deposition properties of the composition. Optional components include but are not limited to botanicals, chelators, humectant skin or hair conditioners, lubricants, moisture barriers/emollients, opacifiers, preservatives (dimethyldimethylol hydantoin, methylchloroisothiazolinone/methylisothiazolinone, sodium benzoate), spreading aids, conditioning polymers, vitamins, viscosity adjusters (natural and synthetic), suspended beads, enzymes, electrolytes (e.g., KCl, NaCl), hydrotropes (e.g., ethanol, sodium xylene sulfonate, and sodium cumene sulfonate), inorganics (e.g., clay, bentonite, kaolin), particulate materials, color additives (e.g., pigments and dyes), as well as the numerous other optional components for enhancing and maintaining the properties and aesthetics of the personal care deposition compositions. Such components are also described in detail in well-known sources such as Mitchell C. Schlossman, *The Chemistry and Manufacture of Cosmetics*, Volumes I and II, Allured Publishing Corporation, 2000.

Methods for preparing the personal care deposition compositions of the present technology include conventional formulation and mixing techniques. Many variations of formulating the deposition compositions exist, and all are considered within the scope of the present technology.

In one aspect, the deposition composition is prepared by a direct mixing process in accordance with method 1.

Method 1 (Direct Formulation)

1) Add the anionic polymer into a main mixing vessel with water and mix until the polymer is homogeneously dispersed.
2) Add the surfactant (e.g., anionic) and preservative to the main vessel and mix until homogeneously dispersed.
3) In a separate vessel combine the ampholytic polymer and optional second surfactant (e.g., zwitterionic/amphoteric) and mix until homogeneously dispersed.
4) Add the ampholytic polymer/surfactant mixture to the main mixing vessel and mix until homogeneously dispersed.
5) Optionally, adjust pH to the desired value with an acidic or basic pH adjusting agent.
6) Add lipophilic component to the main mixing vessel with mixing until homogeneously dispersed.
7) Add optional electrolyte to the main mixing vessel and mix until homogeneously dispersed.

In one aspect, the deposition composition can be formulated by first preparing a concentrate of the ampholytic and anionic polymers and subsequently formulating the desired product from the concentrate as set forth in method 2. In this process the concentrate may be used to immediately formulate the desired personal care deposition composition, or the concentrate may be stored for an indefinite period and later used to formulate a desired personal care deposition composition.

Method 2 (Formulation from a Concentrate)

1) In a first vessel, add water, ampholytic polymer and optional electrolyte (e.g., NaCl) and mix until a homogeneous dispersion is obtained.
2) Add the optional natural anionic polymer to the first vessel and mix until homogeneously dispersed.
3) To a second vessel add powdered anionic polymer and lipophilic material and mix until a homogeneous dispersion is obtained. Add the mixture prepared in the second vessel to the first vessel and mix until a homogeneous dispersion is obtained.
4) Optionally, adjust pH to a desired value with an acidic or basic pH adjusting agent.
5) Store the concentrate until needed.
6) To formulate a personal care deposition composition from the concentrate prepared in steps 1 to 5 above, add water and the desired amount of concentrate to a mixing vessel and mix until a homogeneous dispersion is obtained.
7) Add the desired surfactant and preservative to the mixing vessel and mix until homogeneously dispersed.
8) Add optional second surfactant to the mixing vessel and mix until homogeneously dispersed.
9) Adjust pH to the desired value with an acidic or basic pH adjusting agent.
10) Add additional lipophilic material in an amount to obtain the desired final lipophilic concentration in the formulation to the mixing vessel and mix until homogeneously dispersed.
11) Add electrolyte to the mixing vessel and mix with the contents until dispersed.

The lipophilic material or blends thereof can be added at anytime during the formulation of the of the personal care deposition compositions described in the protocols for Method 1 and Method 2 or by any suitable method known to the skilled formulator. The personal care deposition compositions of the present technology may be post added to existing commercially available personal care formulations.

The present technology is exemplified by the following examples that are illustrational and are not to be regarded as limiting the scope of the technology or the way it can be practiced. Unless otherwise specified in the specification and claims, weights are based on 100 percent active material. Any ingredient not supplied as 100 percent active material is identified by the active material percentage. To calculate the amount of active ingredient utilized in any of the exemplified compositions, multiply the listed active material percentage by the amount (as supplied) for an ingredient.

| Component (Supplier) | Chemical Name | Active % | Function |
|---|---|---|---|
| D.I. Water (Lab Grade) | Deionized Water | — | Diluent |
| Carbopol ™ Ultrez-20 Polymer (Lubrizol Advanced Materials, Inc.) | INCI: Acrylates/ C10-30 Alkyl Acrylate Crosspolymer | 100 | Anionic Polymer |
| Carbopol ™ 980 Polymer (Lubrizol Advanced Materials, Inc.) | INCI: Carbomer (crosslinked poly (acrylic acid) | 100 | Anionic Polymer |
| Arbalon ™ R-50 Liquid Cellulose (C.P. Kelco) | INCI: Glycerin (and) Cellulose (and) Cellulose Gum | 100 | Natural Anionic Polymer |
| Sulfochem ™ ES-2PSB Surfactant (Lubrizol Advanced Materials, Inc.) | INCI: Sodium Laureth Sulfate (2 moles of ethoxylation) | 27 | Anionic Surfactant |
| Chembetaine ™ CAD Surfactant (Lubrizol Advanced Materials, Inc.) | INCI: Cocoamido-propyl Betaine | 29.5 | Zwitterionic Surfactant |
| Merquat ™ 550 Polymer (Lubrizol Advanced Materials, Inc.) | INCI: Poly-quaternium-7 | 9.2 | Cationic Polymer |
| Merquat ™ 5 Polymer (Lubrizol Advanced Materials, Inc.) | INCI: Poly-quaternium-5 | 100 | Cationic Polymer |
| Merquat ™ 2003PR Polymer (Lubrizol Advanced Materials, Inc.) | INCI: Poly-quaternium-53 | 21 | Ampholytic Polymer |

-continued

| Component (Supplier) | Chemical Name | Active % | Function |
|---|---|---|---|
| Merquat ™ 295 Polymer (Lubrizol Advanced Materials, Inc.) | INCI: Poly-quaternium-22 | 37.5 | Ampholytic Polymer (anionic: cationic mole ratio of 1:19) |
| Merquat ™ 2001 Polymer (Lubrizol Advanced Materials, Inc.) | INCI: Poly-quaternium-47 | 21 | Ampholytic Polymer |
| Sunflower Oil (Make Your Own Cosmetics) | Sunflower Oil | 100 | Lipophilic Material |
| Sodium Benzoate (VWR International) | Sodium Benzoate | 100 | Preservative |
| Krathon ™ CG Preservative (DuPont Chemical) | INCI: Methylchloro-isothiazolinone Methyliso-thiazolinone | 100 | Preservative |
| Sodium Chloride (VWR International) | Sodium Chloride | 100 | Electrolyte |
| Sodium Hydroxide (VWR International) | Sodium Hydroxide (aqueous) | 20 | pH Adjusting Agent |
| Citric Acid (VWR International) | Citric Acid (aqueous) | 50 | pH Adjusting Agent |
| D&C Red 17 (Orco) | D&C Red 17 (oil soluble) | 100 | Lipophilic Dye |
| D&C Green 5 (Spectra Colors) | D&C Green 5 | 1 | Dye |

Examples 1 and 2

Deposition compositions were formulated by Methodology 1 (Direct Formulation) using the components set forth in Table 1.

TABLE 1

| Components (wt. %) | Ex. 1[1] | Ex. 2 |
|---|---|---|
| DI Water | 39.10 | 39.32 |
| Sulfochem ™ ES-2PSB Surfactant (28%)[2] | 35.61 (≈10% active material) | 35.81 (≈10% active material) |
| Chembetaine ™ CAD (29.5%)[2] | 16.95 (≈5% active material) | 17.05 (≈5% active material) |
| Merquat ™ 295 (37.5)[2] | 1.3 (≈0.5% active material) | 1.3 (≈0.5% active material) |
| Kathon ™ CG Preservtive | 0.10 | 0.10 |
| Citric Acid (50%)[2] | 0.75 (0.375% active material) | — |
| Merquat ™ 2001 Polymer (21)[2] | 1.11 (≈0.2% active material) | 1.11 (≈0.2% active material) |
| Sunflower Oil | 5.03 | 5.06 |
| D&C Red 17 | 0.05 | 0.05 |
| Carbopol ™ Ultrez 20 Polymer | — | 0.2 |
| pH | 4.00 | 3.84 |

[1]Comparative Example
[2]Component used as supplied

Example 3

The deposition compositions of Examples 1 and 2 were applied to a keratinous substrate and evaluated to determine the relative amount of deposition of a lipophilic red dye (D&C Red 17) onto treated substrates. The red dye functions as a visual marker for lipophilic deposition. Higher intensities of red color on the substrate is indicative of higher oil deposition levels on the substrate.

Worsted gabardine wool swatches (2×2 inches) obtained from Testfabrics, Inc. was utilized as the keratinous substrate. 1 ml of D.I. water was applied to the top of each swatch with rubbing by the index finger until the water was evenly distributed on the swatches. Approximately 0.20 g of the deposition compositions of Examples 1 and 2 was weighed into 1 ml syringes and applied to the top of wetted swatches. The treated swatches were held in the palm of the hand and the index finger on the opposite hand was used to rub the sample into the wet wool swatches for 30 seconds. A combination of a circular rubbing motion and a back-and-forth rubbing motion was used to distribute the deposition composition evenly across the entire wool swatch. The treated swatches were rinsed by holding the swatch vertically under a running tap water stream (37-38° C.; 1 gallon/min flow rate) for 15 seconds. The treated swatches were dried on wire mesh rack overnight at ambient room temperature (approximately 20-25° C.) before a qualitative visual analysis of dye deposition was conducted.

Results indicated that the deposition compositions containing a combination of ampholytic and anionic polymers (composition of Example 2) exhibited more intensive red dye deposition onto the keratinous wool substrate compared to the composition containing an ampholytic polymer but no anionic polymer component (composition of Example 1).

Examples 4 and 5

Deposition compositions were formulated by Methodology 1 (Direct Formulation) using the components set forth in Table 2.

TABLE 2

| Components (wt. %) | Ex. 4 | Ex. 5[2] |
|---|---|---|
| DI Water | 47.7 | 48.89 |
| Carbopol ™ 980 Polymer | 0.2 | 0.2 |
| Sulfochem ™ ES-2PSB Surfactant (28%)[1] | 32.08 (≈9% active material) | 32.17 (≈9% active material) |
| Sodium Benzoate | 0.50 | 0.50 |
| Chembetaine ™ CAD Surfactant (29.5%)[1] | 10.15 (≈3% active material) | 10.18 (≈3% active material) |
| Merquat ™ 2003PR Polymer (21%)[1] | 2.37 (≈0.5% active material) | — |
| Merquat ™ 295 Polymer (37.5%)[1] | — | 1.33 (≈0.5% active material) |
| D&C Green 5 (1%)[1] | 0.33 (≈0.003% active material) | 0.33 (≈0.003% active material) |
| Sunflower Oil | 5.12 | 5.12 |
| D&C Red 17 | 0.02 | 0.02 |
| NaCl | 1.27 | 1 |
| NaOH (20% aqueous)[1] | 0.26 | 0.26 |

TABLE 2-continued

| Components (wt. %) | Ex. 4 | Ex. 5[2] |
|---|---|---|
| | (≈0.05% active material) | (≈0.05% active material) |
| pH | 5.39 | 5.5 |

[1]Component used as supplied
[2]Comparative Example

Example 6

The deposition compositions of Examples 4 and 5 were applied to keratinous wool substrates prepared and treated as set forth in Examples 3, except that 0.25 g of the exemplified deposition composition was applied to each swatch and the treated swatches were subjected to horizontal rinsing (relative to the tap water stream) for 7 seconds instead of vertical rinsing for 30 seconds. The treated swatches were evaluated to determine the amount of oil deposited onto the substrate by Attenuated Total Reflection—Fourier Transform Infrared Spectroscopy (ATR-FTIR).

To determine the amount of lipophilic material onto deposited swatches, the treated swatches were analyzed on an ATR-FTIR spectrometer (Bruker model Alpha). Treated swatches were separately placed on the diamond crystal of the spectrometer and infrared light was reflected off the surface to give a composition profile of the swatch and materials deposited onto the swatch. The position of the swatch was moved relative to the measuring crystal to obtain readings from 3 different locations on each swatch. Baseline peaks were determined to calculate peak heights at known dominant peaks for the oil. For determination of oil deposited, the carbonyl peak (1738 $cm^{-1}$), which is the dominant peak in most seed oils. The carbonyl peak was then ratioed to the amide II peak (1537 $cm^{-1}$) as a normalization peak. The carbonyl/amide II ratio was used to qualitatively compare deposition between samples. A higher carbonyl/amide II ratio is indicative of more lipophile (oil) deposition onto the substrate.

TABLE 3

| Composition | Average Carbonyl/Amide II Ratio |
|---|---|
| Ex. 4 | 0.0113 |
| Ex. 5[1] | −0.006 |

[1]Comparative Example

The deposition composition of Example 4 comprising an anionic/ampholytic polymer combination exhibits higher oil deposition onto the keratinous substrate compared to the composition of Example 5 comprising an anionic/amphoteric polymer combination where the ampholytic polymer has an anionic:cationic residue mole ratio of 1:19. In other words, the ampholytic polymer of Example is highly cationic in nature (95 mole % cationic residues and 5% anionic residues).

Example 7

A concentrate containing the components set forth in Table 4 was prepared and subsequently utilized to formulate the final product deposition compositions of Examples 8 and 9 via Methodology 2.

TABLE 4

| Components (grams) | Ex. 7[1] |
|---|---|
| DI Water | 0.79 |
| Arbalon ™ R-50 Liquid Cellulose | 1.0 |
| Carbopol 980 | 0.1 |
| Merquat 2003PR (21%)[2] | 2.4 (≈0.5% active material) |
| Sunflower Oil | 1 |
| Sodium Chloride | 0.5 |

[1]Concentrate (prepared by methodology 2)
[2]Component used as supplied

To formulate the final product, the concentrate prepared in Example 7 was utilized as a base formulation to which the additional components listed in Table 5 were added. The comparative compositions of Examples 10 and 11 were formulated in accordance with components listed in Table 5 and methodologies set forth in Examples 2a (E7) and 4b (E12), respectively, of U.S. Pat. No. 10,159,638.

TABLE 5

| Components (wt. %) | Ex. 8[1] | Ex. 9[1] | Ex. 10[2] | Ex. 11[2] |
|---|---|---|---|---|
| DI Water | 45.81 | 60.31 | 43.6 | 64.0 |
| Concentrate from Ex. 7 | 5.79 | 5.79 | — | — |
| Carbopol ™ 980 Carbomer | — | — | 0.1 | 0.1 |
| Sulfochem ™ ES-2PSB Surfactant (28%)[3] | 32.1 (≈9% active material) | 12.5 (3.5% active material) | 32.1 (≈9% active material) | 12.5 (3.5% active material) |
| Sodium Benzoate | 0.5 | 0.5 | 0.5 | 0.5 |
| Chembetaine ™ CAD Surfactant (29.5%)[3] | 6.8 (≈20% active material) | 11.9 (≈3.5% active material) | 6.8 (≈20% active material) | 11.9 (≈3.5% active material) |
| Merquat ™ 550 Polymer (9.2%)[3] | — | — | 6.5 (≈0.6% active material) | — |
| Merquat ™ 5 Polymer | — | — | — | 0.60 |
| Sunflower Oil | 9 | 9 | 10.0 | 10.0 |
| Sodium Chloride | — | — | 0.4 | 0.4 |

[1]Prepared by Methodology 2
[2]Comparative
[3]Component used as supplied

Example 12

The compositions of Examples 8 to 11 were applied to wool swatches which were analyzed by ATR-FTIR spectroscopy pursuant to the methodology set forth in Example 6. The carbonyl/amide II ratio was used to qualitatively compare oil deposition between samples. Results are presented in Table 6. Each value represents an average of 5 measurements taken from different locations on each swatch.

TABLE 6

| Composition | Average Carbonyl/Amide II Ratio |
|---|---|
| Ex. 8 | 0.136 |
| Ex. 9 | 0.114 |
| Ex. 10[1] | 0.052 |
| Ex. 11[1] | 0.055 |

[1]Comparative Example

The deposition composition of Examples 8 and 9 comprising an anionic/ampholytic polymer combination exhibits higher oil deposition onto a keratinous substrate compared to the compositions of Examples 10 and 11 comprising an anionic/cationic polymer combination.

What is claimed is:

1. A personal care composition for depositing a lipophilic material onto a keratinous substrate comprising:

a) from about 0.03 to about 2 wt. %, or from about 0.1 to about 0.8 wt. %, or from about 0.2 to about 0.6 wt. % of at least one ampholytic polymer;

b) from about 0.01 to about 2 wt. %, or from about 0.05 to about 0.5 wt. %, or from about 0.1 to about 0.3 wt. % of at least one synthetically derived anionic polymer;

c) from about 0.01 wt. % to about 45 wt. %, or from about 0.05 to about 40 wt. %, or from about 0.1 to about 30 wt. %, or from about 0.5 to about 25 wt. %, or from about 1 to about to about 20 wt. %, or from about 3 to about 15 wt. %, or from about 5 to about 10 wt. % of at least one lipophilic material;

d) from about 30 to about 95 wt. %, or from about 50 to about 90 wt. %, or from about 70 to about 85 wt. % water;

e) from about 0.01 to about 2 wt. %, or from about 0.05 to about 0.5 wt. %, or from about 0.1 to about 0.3 wt. %, of a naturally derived anionic polymer;

wherein the weight ratio of ampholytic polymer to anionic polymer (synthetically derived and naturally derived) is from about 10:1 to about 1:1, or from about 7:1 to about 2:1, or from about 5:1 to about 3:1; and wherein all weight percent ranges are based on the total weight of the composition and the sum of all components total 100 wt. %.

2. A personal care composition of claim 1, further comprising from about 5 to about 30 wt. %, or from about 7 to about 25 wt. %, or from about 9 to about 20 wt. % of at least one surfactant selected from anionic, cationic, zwitterionic, nonionic, and mixtures thereof.

3. A personal care composition of claim 2, wherein said at least one surfactant is anionic.

4. A personal care composition of claim 2, wherein said at least one surfactant is selected from wherein said anionic surfactant is present and is selected from alkyl sulfates, alkyl ether sulfates, alkyl sulphonates, alkaryl sulfonates, α-olefin-sulphonates, alkylamide sulphonates, alkarylpolyether sulphates, alkylamidoether sulfates, alkyl monoglyceryl ether sulfates, alkyl monoglyceride sulfates, alkyl monoglyceride sulfonates, alkyl succinates, alkyl sulfosuccinates, alkyl ether sulfosuccinates, alkyl sulfosuccinamates, alkyl amidosulfosuccinates; alkyl sulfoacetates, alkyl phosphates, alkyl ether phosphates, alkyl ether carboxylates, alkyl amidoethercarboxylates, acyl lactylates, alkyl isethionates, acyl isethionates, alkyl sarcosinates, carboxylate salts and amino acid derived surfactants such as N-alkyl amino acids, N-acyl amino acids, alkyl peptides, fatty acid soaps, and mixtures thereof.

5. A personal care composition of claim 1, further comprising at least one zwitterionic and/or amphoteric surfactant.

6. A personal care composition of claim 5, wherein said at least one zwitterionic and/or amphoteric surfactant is selected from alkyl betaines; alkylamido betaines; alkylamido sultaines; alkyl mono- and di-amphocarboxylates; amine oxides; and mixtures thereof.

7. A personal care composition of claim 1, wherein said ampholytic polymer comprises residues of i) at least one cationic monomer, ii) at least one anionic monomer; and optionally iii) at least one nonionic monomer.

8. A personal care composition of claim 1, wherein the amount of cationic monomer residues is equal to or greater than the amount of anionic monomer residues in in said ampholytic polymer.

9. A personal care composition of claim 1, wherein the mole ratio of anionic monomer residues to cationic monomer residues in said ampholytic polymer ranges from about 1:15 to about 3:1, or from about 1:10 to about 2:1, or from about 1:5 to 1:1.

10. A personal care composition of claim 1, wherein said ampholytic polymer comprises a cationic monomer residue selected from diallyldimethylammonium chloride (DADMAC), acrylamidopropyltrimethyl ammonium chloride (APTAC) methacrylamidopropyltrimethylammonium chloride (MAPTAC), and mixtures thereof.

11. A personal care composition of claim 1, wherein said ampholytic polymer comprises an anionic monomer residue selected from acrylic acid (AA), methacrylic acid (MAA), 2-acrylamido-2-methylpropane sulfonic acid (AMPSA) or 2-methacrylamido-2-methylpropane sulfonic acid (MAMPSA), acrylamidomethylpropyl sulfonic acid; and salts thereof; and mixtures thereof.

12. A personal care composition of claim 1, wherein the mole percentage of anionic monomer residues to cationic monomer residues in said ampholytic polymer is about 36:64 to about 64:36.

13. A personal care composition of claim 1, wherein said ampholytic polymer comprises a nonionic monomer residue selected from methyl acrylate, methyl methacrylate, acrylamide, methacrylamide, and mixtures thereof.

14. A personal care composition of claim 1, wherein the mole ratio of nonionic monomer residues to the combined anionic and cationic monomer residues in said ampholytic polymer ranges from about 1:20 to about 9:1, or from about 3:7 to about 7:3, or from about 4:6 to about 6:4.

15. A personal care composition of claim 1, wherein said ampholytic polymer is selected from poly(diallyldimethylammonium chloride-co-acrylic acid), poly(acrylamide-co-acrylic acid-co-diallyldimethylammonium chloride), poly (acrylamide-co-acrylic acid-co-methacrylamidopropyltrimethyl ammonium chloride), poly(methyl acrylate-co-acrylic acid-co-methacrylamidopropyltrimethyl ammonium chloride) and mixtures thereof.

16. A personal care composition of claim 1, wherein said ampholytic polymer further comprises a nonionic monomer residue and the mole percentage of nonionic monomer residues to anionic monomer residues to cationic monomer residues is from about 10 to about 50 mole percent nonionic; from about 10 to about 50 mole percent anionic; and from about 25 to about 45 mole percent cationic.

17. A personal care composition of claim 1, wherein said at least one synthetically derived anionic polymer is prepared from one or more ethylenically unsaturated $C_3$-$C_6$ carboxylic acid containing monomers.

18. A personal care composition of claim 1, wherein said at least one synthetically derived anionic polymer is prepared from one or more monomers selected from acrylic acid, methacrylic acid, itaconic acid, citraconic acid, maleic acid, maleic anhydride, fumaric acid, crotonic acid, aconitic acid, salts thereof, and mixtures thereof.

19. A personal care composition of claim 1, wherein said at least one synthetically derived anionic polymer is prepared from one or more ethylenically unsaturated $C_3$-$C_6$ carboxylic acid containing monomers and one or more monomers of formula (I) and/or formula (II):

(I)

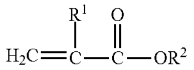

(II)

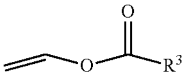

wherein $R^1$ is hydrogen, methyl or ethyl and $R^2$ is an alkyl group containing 1 to 30 carbon atoms.

20. A personal care composition of claim 1, wherein said at least one synthetically derived anionic polymer is prepared with an ethylenically polyunsaturated crosslinking monomer.

21. A personal care composition of claim 1, wherein said synthetically derived anionic polymer is a homopolymer of (meth)acrylic acid.

22. A personal care composition of claim 1, wherein said anionic polymer is a copolymer of (meth)acrylic acid and a comonomer selected from a $C_1$-$C_{30}$ alkyl (meth)acrylate, a vinyl ester of a $C_1$-$C_{22}$ carboxylic acid.

23. A personal care composition of claim 1, wherein said synthetically derived anionic polymer is selected from Carbomer, Acrylates/C10-30 Alkyl Acrylate Crosspolymer, Acrylates Copolymer, Acrylates Crosspolymer-4, Acrylates/Vinyl Neodecanoate Crosspolymer, Sodium Polyacrylate, and mixtures thereof.

24. A personal care composition of claim 1, wherein said naturally derived anionic polymer is selected from cellulose gum, xanthan gum, dehydroxanthan gum, carboxymethylcellulose, acacia gum, gum Arabic, alginic acid, gum karya, gum tragacanth, diutan gum, carrageenan gum, gellan gum, and mixtures thereof.

25. A personal care composition of claim 1, wherein said at least one lipophilic material is selected from essential oils, fragrance oils, ester oils, glyceride oils, plant oils, fatty alcohols, ethoxylated fatty alcohols, fatty acids, silicone oils, mineral oils, petrolatum, plant waxes, plant butters, water insoluble or slightly soluble organic sunscreens, micronized sunscreens, plant extracts, hydrophobically modified pigments, hydrophobic vitamin or vitamin complexes, antioxidants, antifungal agents, anti-inflammatory actives, antimicrobials, antiperspirant actives, deodorant actives, skin health actives, and mixtures thereof.

26. A personal care deposition agent concentrate comprising:

a) from about 0.5 to about 50 wt. %, or from about 1 to about 35 wt. %, or from about 3 to about 20 wt. % of at least one ampholytic polymer;

b) from about 0.1 to about 20 wt. %, or from about 0.5 to about 10 wt. %, or from about 1 to about 5 wt. % of at least one anionic polymer;

c) from about 0.01 wt. % to about 45 wt. %, or from about 0.05 to about 40 wt. %, or from about 0.1 to about 30 wt. %, or from about 0.5 to about 25 wt. %, or from about 1 to about to about 20 wt. %, or from about 3 to about 15 wt. %, or from about 5 to about 10 wt. % of at least one lipophilic material; and d) from about 1 to about 80 wt. %, or from about 10 to about 70 wt. %, or from about 20 to about 60 wt. % water, and e) a naturally derived anionic polymer;

wherein the weight ratio of ampholytic polymer to anionic polymer (synthetically derived and naturally derived) is from about 10:1 to about 1:1, or from about 7:1 to about 2:1, or from about 5:1 to about 3:1; and wherein all weight percent ranges are based on the total weight of the composition and the sum of all components total 100 wt. %.

27. A personal care deposition agent concentrate of claim 26, wherein said ampholytic polymer is selected from poly (diallyldimethylammonium chloride-co-acrylic acid), poly (acrylamide-co-acrylic acid-co-diallyldimethylammonium chloride), poly(acrylamide-co-acrylic acid-co-methacrylamidopropyltrimethyl ammonium chloride), poly(methyl acrylate-co-acrylic acid-co-methacrylamidopropyltrimethyl ammonium chloride), and mixtures thereof.

28. A personal care deposition agent concentrate of claim 26, wherein said at least one synthetically derived anionic polymer is selected from Carbomer, Acrylates/C10-30 Alkyl Acrylate Crosspolymer, Acrylates Copolymer, Acrylates Crosspolymer-4, Acrylates/Vinyl Neodecanoate Crosspolymer, Sodium Polyacrylate, and mixtures thereof.

29. A personal care deposition agent concentrate of claim 26, wherein said at least one derivatized naturally derived anionic polymer is selected from carboxymethylcellulose.

30. A personal care deposition agent concentrate of claim 26, wherein said at least one lipophilic material is selected from essential oils, fragrance oils, ester oils, glyceride oils, plant oils, fatty alcohols, ethoxylated fatty alcohols, fatty acids, silicone oils, mineral oils, petrolatum, plant waxes, plant butters, water insoluble or slightly soluble organic sunscreens, micronized sunscreens, plant extracts, hydrophobically modified pigments, hydrophobic vitamin or vitamin complexes, antioxidants, antifungal agents, anti-inflammatory actives, antimicrobials, antiperspirant actives, deodorant actives, skin health actives, and mixtures thereof.

31. A personal care composition of claim 26, wherein the naturally derived anionic polymer is selected from the group consisting of cellulose gum, xanthan gum, dehydroxanthan gum, carboxymethylcellulose, acacia gum, gum Arabic, alginic acid, gum karya, gum tragacanth, and mixtures thereof.

* * * * *